US012631607B2

(12) United States Patent　　　　(10) Patent No.:　US 12,631,607 B2
König　　　　　　　　　　　　　　　　(45) Date of Patent:　　May 19, 2026

(54) METHOD AND DEVICE FOR COMPENSATING TEMPERATURE CHANGE RATE DEPENDENT EFFECTS

(71) Applicant: TDK Corporation, Tokyo (JP)

(72) Inventor: Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 325 days.

(21) Appl. No.: 18/350,434

(22) Filed: Jul. 11, 2023

(65) Prior Publication Data

US 2023/0349877 A1　　Nov. 2, 2023

Related U.S. Application Data

(63) Continuation-in-part of application No. 17/504,267, filed on Oct. 18, 2021, now Pat. No. 11,740,175.

(30) Foreign Application Priority Data

Oct. 19, 2020　(DE) ......................... 102020127455.6

(51) Int. Cl.
　　*G01N 33/00*　　　(2006.01)
　　*G01N 33/18*　　　(2006.01)
(52) U.S. Cl.
　　CPC ..... *G01N 33/0006* (2013.01); *G01N 33/0068* (2024.05)
(58) Field of Classification Search
　　CPC ........... G01N 33/0006; G01N 33/0062; G01N 33/0068; G01N 25/18; G01N 25/00;

G01N 25/02; G01N 25/16; G01N 25/20; G01N 21/274; G01N 21/3504; G01N 27/3274; G01N 27/18; G01N 15/1429
USPC .... 73/861.356, 1.06, 204.19, 23.2; 324/105; 700/109, 48, 110; 702/24, 104, 189, 130, 702/182, 99, 85, 183, 127; 703/2, 5
See application file for complete search history.

(56) References Cited

U.S. PATENT DOCUMENTS

| | | |
|---|---|---|
| 7,244,939 B2 | 7/2007 | Stuttard |
| 2011/0023459 A1* | 2/2011 | Nieuwstadt ......... F02D 41/2441 |
| | | 60/285 |
| 2013/0301052 A1* | 11/2013 | MacGregor ............ G01N 21/27 |
| | | 356/437 |
| 2018/0348311 A1 | 12/2018 | Voss et al. |
| 2020/0348134 A1 | 11/2020 | Katingari et al. |
| 2022/0381731 A1* | 12/2022 | Rogers ............... G01N 27/4163 |

FOREIGN PATENT DOCUMENTS

| | | | | |
|---|---|---|---|---|
| EP | 0651244 A1 * | 5/1995 | ........ | G01N 21/3504 |
| EP | 1605252 B1 * | 2/2019 | ........ | G01N 21/3504 |
| JP | 2001523317 A * | 11/2001 | ........ | G01N 21/3504 |
| WO | WO-2012059743 A2 * | 5/2012 | ........... | G01N 21/274 |

\* cited by examiner

*Primary Examiner* — Jeffrey P Aiello
(74) *Attorney, Agent, or Firm* — Slater Matsil, LLP

(57)　　　　　ABSTRACT

A method of analysing a variation in a gas concentration signal and setting up an error correction function to compensate for the temperature-change-rate-dependent gas concentration signal is provided. The method includes variating a change rate of the temperature, and measuring a resulting variation in a gas concentration signal.

5 Claims, 4 Drawing Sheets

° CO2 cal [ppm] - Plot 0
○ CO2 gradient eliminated [ppm] - Plot 0
● T [°C] - Plot 0

METHOD AND DEVICE FOR COMPENSATING TEMPERATURE CHANGE RATE DEPENDENT EFFECTS

CROSS-REFERENCE TO RELATED APPLICATIONS

This application is a Continuation in Part and claims the benefit of U.S. application Ser. No. 17/504,267, filed on Oct. 18, 2021 which application claims priority to German Patent Application No. 102020127455.6, filed on Oct. 19, 2020, which application is hereby incorporated herein by reference.

TECHNICAL FIELD

Special types of gas sensors, e.g., thermal conductivity type sensors can show a temperature gradient dependence. That means that the output signal of the gas sensor not only depends on the gas concentration, e.g., $CO_2$ but also depends on the change rate (gradient) of the temperature.

BACKGROUND

In the state of the art such a behavior is not compensated. Or alternatively, a measurement unit is heated to a constant temperature so that no gradient will occur. This can mean in particular that no change in temperature occurs.

SUMMARY

Embodiments provide a method for compensating temperature gradient effects for gas concentration sensors comprising the following steps:
    variating a temperature gradient,
    measuring the variation of gas concentration depending on the variation of the temperature gradient,
    analysing the dependence of gas concentration and temperature gradient for setting up an error correction function,
    applying the error correction function to correct measured values of gas concentration. The temperature gradient may, in particular, be understood as change rate of the temperature.

As another embodiment, a method for setting up an error correction function to compensate for a temperature-change-rate-dependent gas concentration signal variation is provided. The method includes the following steps:
    variating a change rate of the temperature,
    measuring a resulting variation in a gas concentration signal in dependence of the variation in the change rate of the temperature,
    analysing this variation in the gas concentration signal and setting up an error correction function to compensate for the temperature-change-rate-dependent gas concentration signal variation.

Optionally, this method may also include a step of applying the error correction function to correct a measured gas concentration signal.

In the methods above, the error correction function is a linear function.

In one embodiment the dependence of gas concentration and temperature gradient is analysed by a neuronal network. Accordingly, analysing the variation in the gas concentration signal may be carried out by a neuronal network.

Further embodiments provide a device for measuring gas concentrations independent of a temperature gradient comprising:
    a sensor unit measuring gas concentrations,
    an analysing unit arranged to analyse the dependence of gas concentration on the temperature gradient during calibration of the sensor unit in order to set up an error correction function and to apply the error correction function to measured values of gas concentration after calibration is completed.

As another embodiment a device for measuring gas concentrations is provided. The device comprises:
    a sensor unit measuring gas concentrations,
    an analysing unit configured to measure a variation in a gas concentration signal in dependence of a variation in a change rate of the temperature during a calibration of the sensor and to analyse this variation in the gas concentration signal and setting up an error correction function to compensate for the temperature-change-rate-dependent gas concentration signal variation.

In one embodiment, the device is configured to apply the error correction function to correct a measured gas concentration signal In one embodiment the analysing unit comprises a neuronal network analysing the dependence of gas concentration on the temperature gradient. Accordingly, the analysing unit comprises a neuronal network configured to analyse the variation in the gas concentration signal.

BRIEF DESCRIPTION OF THE DRAWINGS

In the following the invention is exemplarily described by using figures. The invention is not limited to the described examples. The figures show:

FIG. 3 shows a different plot of a CO2 concentration output signal during a temperature sweep measured by a different sensor as for FIG. 2.

DETAILED DESCRIPTION OF ILLUSTRATIVE EMBODIMENTS

As mentioned in the introduction special types of gas sensors, e.g., thermal conductivity type sensors can show a temperature gradient dependence. Accordingly, special types of gas sensors, e.g., thermal conductivity type sensors can show a dependence of the measured gas concentration signal on the change rate of the temperature.

Figure 1:
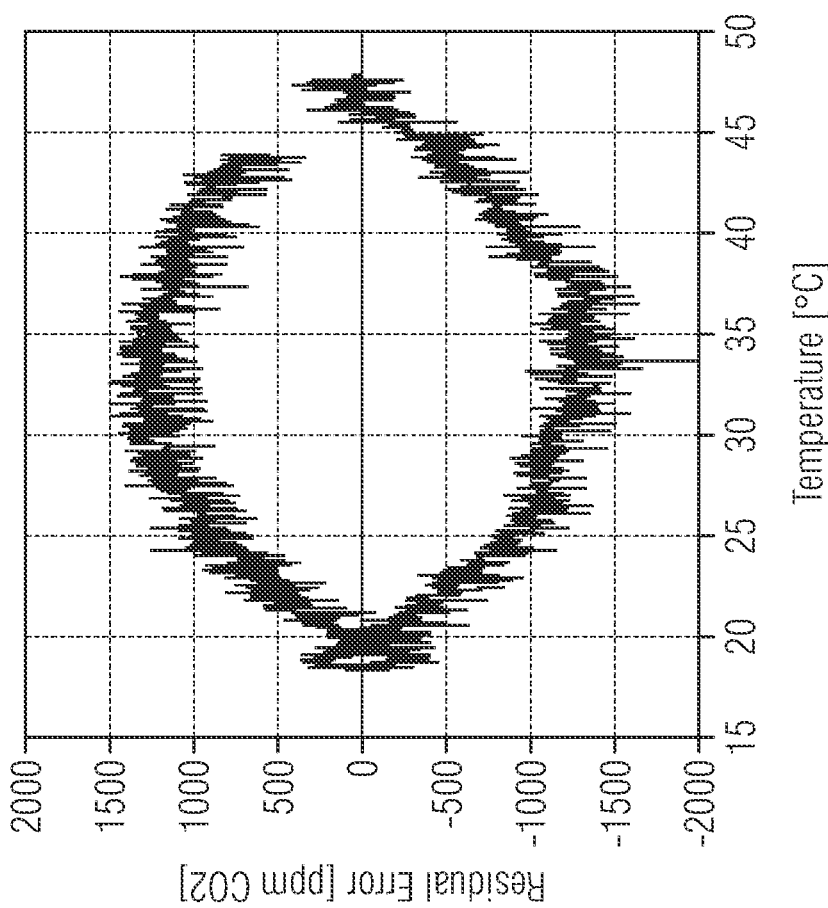
FIG. 1 shows a temperature vs time curve and a residual error vs temperature curve of a measurement by a $CO_2$ thermal conductivity gas sensor.
Figure 1:
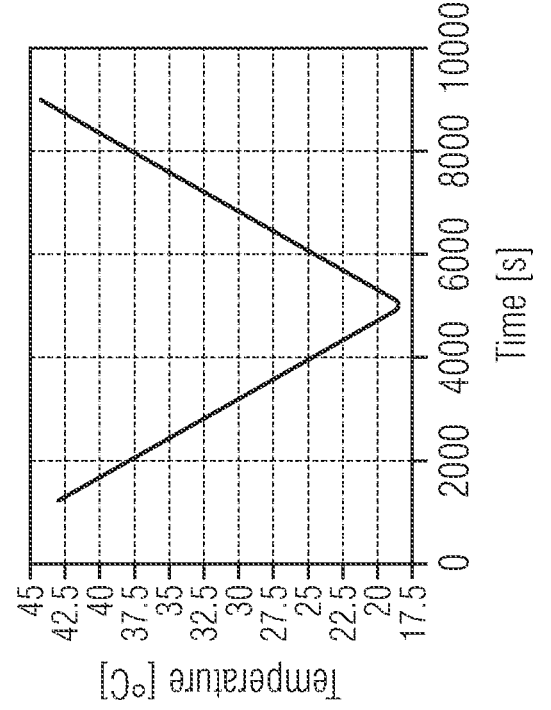

FIG. 1 shows an example for such a dependence. The left diagram shows the temperature sweep that is applied to an exemplary sensor. In the right diagram, the influence of the temperature for this temperature sweep on a $CO_2$ concentration output signal is shown. Other gases would show a similar behavior. It becomes clear from this figure that the output signal does not depend on the absolute value of the temperature. Instead a dependence of the output signal on the gradient (change rate) of the temperature can be observed. In embodiments a method is discussed how to compensate for this behavior. The method employs above observation in order to compensate for this influence on a measured gas concentration signal.

A first approach to account for such dependency is to estimate the gradient drift/error rate (error of the gas concentration value in dependence on the temperature gradient) and subtract it from the output signal (recorded value for the gas concentration).

Figure 2:
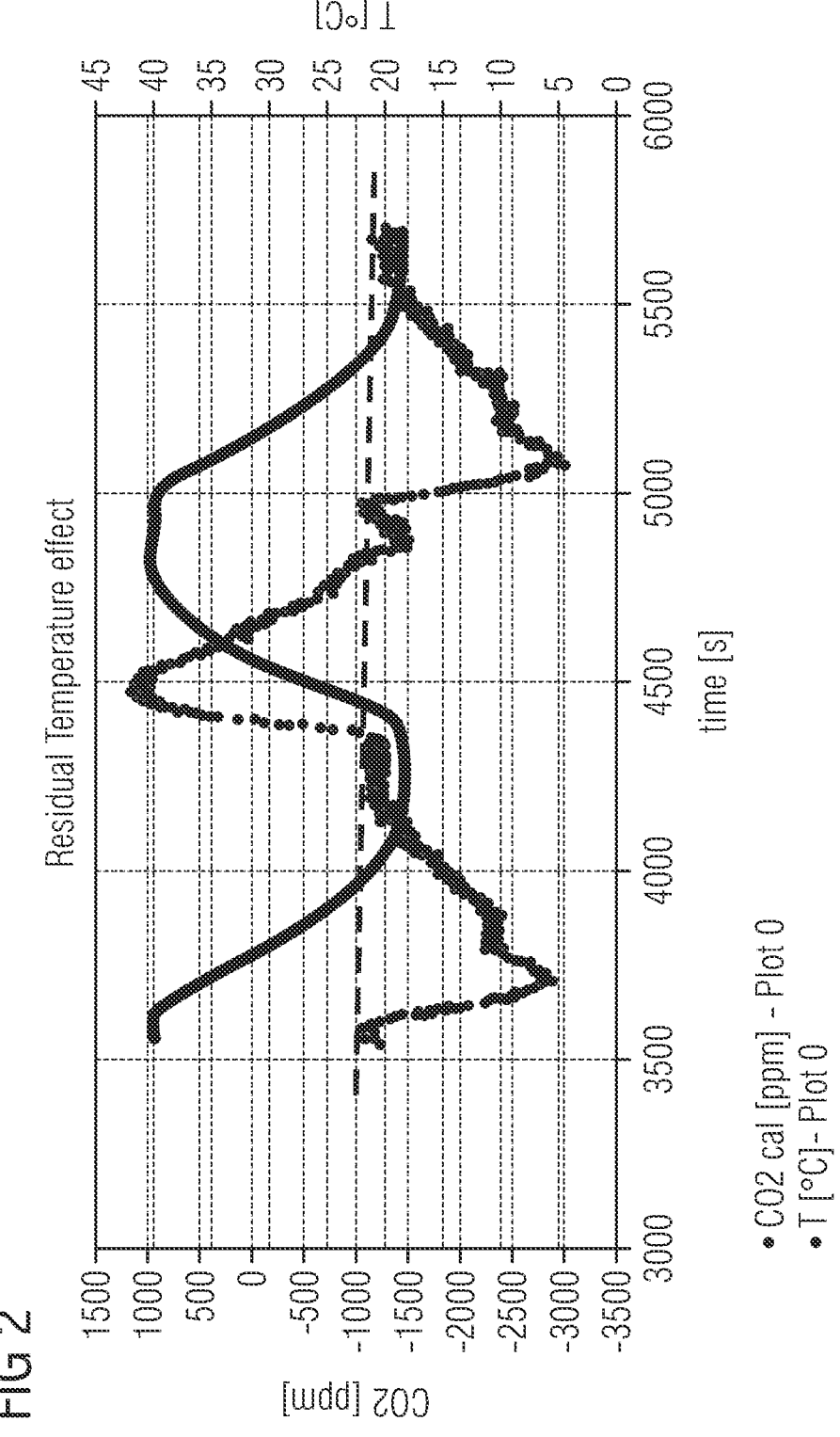
FIG. 2 shows the $CO_2$ concentration output signal during a temperature sweep.

FIG. 2 shows the $CO_2$ concentration output signal during a temperature sweep. It further supports the understanding of the temperature change rate depended error behavior. The darker curve (labeled as T [° C.]—Plot 0) shows the temperature that is changed during the experiment; i.e. it represents the temperature sweep. The other curve (lighter color; labeled as CO2 cal [ppm—Plot 0)] shows the gas sensor output signal (uncompensated measured gas concentration). It is observed that independent of the actual absolute value of the temperature, in regions where the darker curve is flat (for example at the start of the measurement, or in the range about 4250 s, or above 5500 s), the output signal (lighter curve) is stable at about 1000 ppm, which is indicated by the dashed horizontal line. In contrast, it can be seen that at any point, in which a change in the temperature takes place (for example between 3500 and 4000 s, or between 4400 and 4700 s, or between 5000 and 5400 s) the measured signal shows a strong deviation from the dashed line. Furthermore, a dependence of the direction of the deviation from the slope of the temperature curve is observed. In case of a negative slope in the temperature curve (temperature decrease/cooling), the measured signal is below the dashed line, which is defined as a negative gradient error occurring. In case of a positive slope in the temperature curve (temperature increase/heating), the measured signal is above the dashed line, which is defined as a positive gradient error occurring. Please note that overall a minor temporal drift of the signal can be observed as well.

Figure 3:
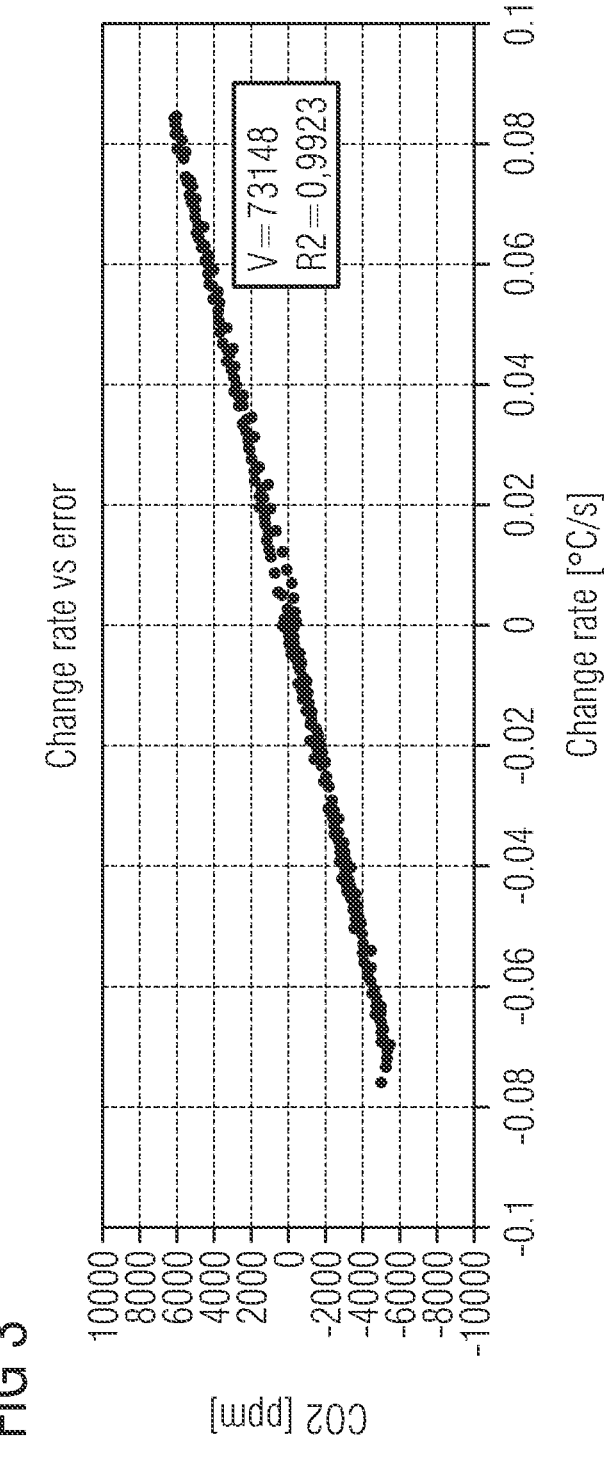
FIG. 3 shows similar data like shown in FIG. 2 but measured by a different sensor. The error of the output signal vs the temperature change rate is shown. Accordingly.

Results of a similar experiment are shown in FIG. 3. For this experiment a similar temperature sweep as for FIG. 2 was conducted and recorded for another sensor. In FIG. 3 the $CO_2$ output signal is plotted against the change rate of the temperature.

FIG. 3 reveals a linear dependence of the deviation or error of the $CO_2$ output signal from the change rate of the temperature.

During a calibration procedure the slope "A" of the gradient error is measured (gradient error=deviation of the $CO_2$ output signal induced by a change in the change rate of the temperature when deviating from a constant temperature). For the example of FIG. 3, the slope "A" is the slope of the graph of FIG. 3. Using this slope "A", the gas concentration output signal can be correct by using the following error correction function:

$$c(CO_{2_{corrected}})=c(CO_{2_{measured}})-f$$

Herein, "$c(CO_{2_{measured}})$" is the recorded $CO_2$ output signal; "$c(CO_{2_{corrected}})$" is the corrected value for the $CO_2$ concentration, "f" is an error correction function which can be addressed as the gradient error. The gradient error can be calculated by:

$$f=\text{gradient}(T)\times A.$$

Herein, "gradient(T)" is the temperature gradient. In an embodiment of this formula the error correction can be calculated via the following formula:

$$f = A \times \frac{dc(CO_{2_{measured}})}{dT}.$$

Herein "A" is the slope of the curve as defined above, "f" is said correction function, $$\frac{dc(CO_{2_{measured}})}{dT}$$

is the change in the recorded $CO_2$ output signal with the temperature.

By applying the error correction function to the measured concentration values, a much more stable signal is received. The result can be seen in FIG. 4.

Figure 4:
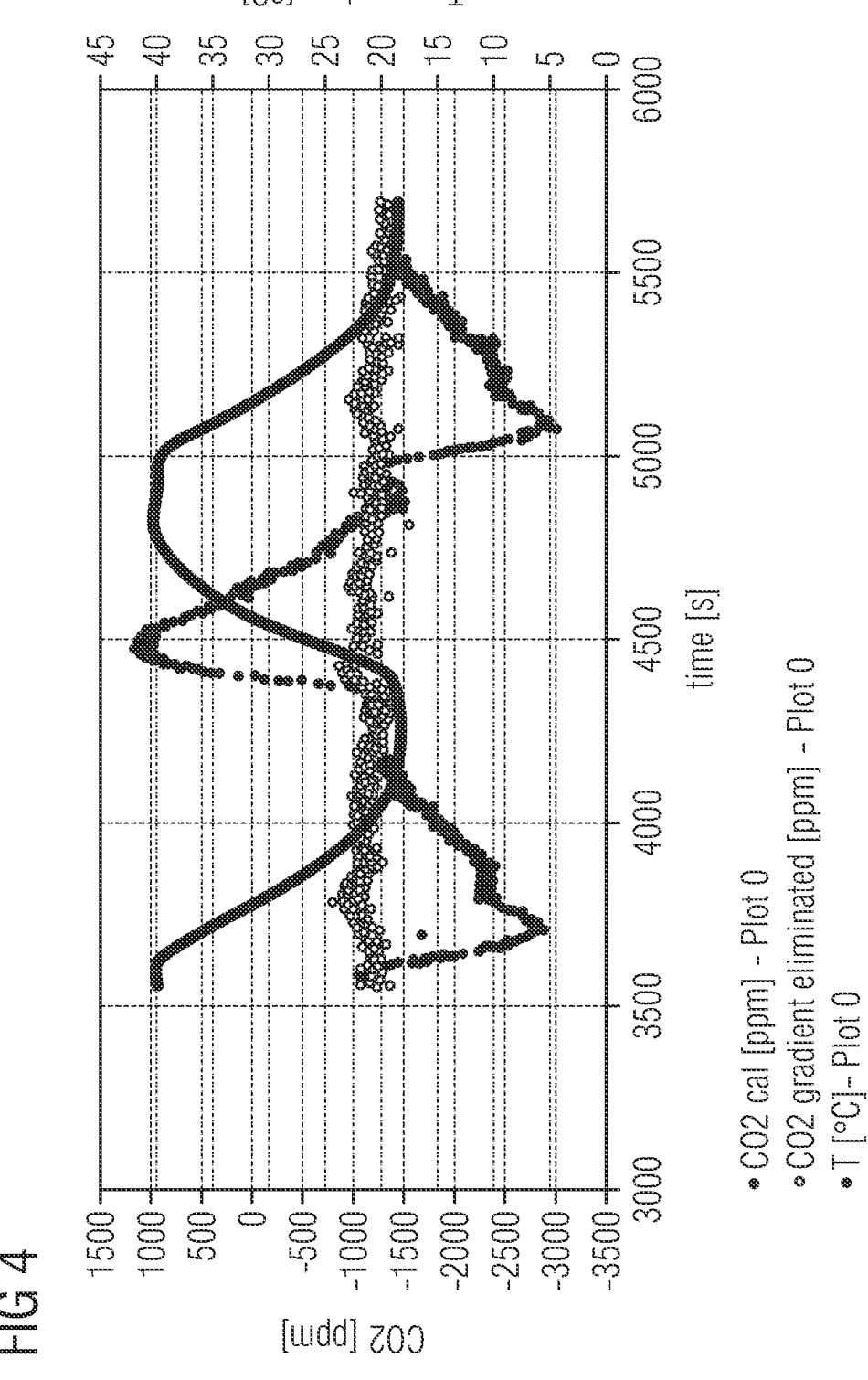
FIG. 4 shows the data set of FIG. 2 and in addition the application of the correction function.

FIG. 4 is based on the same set of data as FIG. 2 and shows the same curves. In addition, it shows the corrected signal for the $CO_2$ concentration. The corrected CO2 concentration values after applying the gradient correction is represented by the lightest curve (labeled as CO2 gradient eliminated [ppm]—Plot 0) in FIG. 4.

It is also possible to use e.g. different or better algorithms to compensate for higher order change rate depended effects. E.g. if the sensor depends on the change of T. For example, a neuronal network can be used to automatically train for such kind of behaviors.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
variating a change rate of a temperature;
measuring a resulting variation in a first gas concentration signal in dependence on the variation in the change rate of the temperature $$\frac{dc_{measured}}{dT};$$

analysing the variation in the first gas concentration signal and setting up an error correction function $$f = A \times \frac{dc_{measured}}{dT};$$

to compensate for a temperature-change-rate-dependent gas concentration signal variation, wherein A is a slope and f is the error correction function;
measuring a second gas concentration signal; and
outputting a concentration of the second gas concentration signal, wherein the concentration is $c_{corrected}$ based on $c_{corrected}=c_{measured}-f$.

2. The method of claim 1, wherein the error correction function is a linear function.

3. The method of claim 1, wherein analysing the variation in the first gas concentration signal is carried out by a neuronal network.

4. A device comprising:

a sensor configured to measure gas concentrations; and an analysing unit configured to:

measure a variation in a first gas concentration signal in dependence on the variation in a change rate of a temperature during a calibration of the sensor $$\frac{dc_{measured}}{dT};$$

and analyse the variation in the gas first concentration signal and set up an error correction function $$f = A \times \frac{dc_{measured}}{dT}$$

to compensate for a temperature-change-rate-dependent gas concentration signal variation, wherein A is a slope and f is the error correction function, wherein the device is configured to output a concentration of a second gas concentration signal, the concentration $c_{corrected}$ being based on the error correction function $$c_{corrected} = c_{measured} - f.$$

5. The device of claim 4, wherein the analysing unit comprises a neuronal network configured to analyse the variation in the first gas concentration signal.

\* \* \* \* \*